(12) United States Patent
Haarer et al.

(10) Patent No.: US 9,835,498 B2
(45) Date of Patent: Dec. 5, 2017

(54) METHOD AND SYSTEM FOR DETERMINING THE CONDITION OF A TIME-TEMPERATURE INDICATOR

(75) Inventors: Dietrich Haarer, Bayreuth (DE); Yoav Lévy, Ramat Hasharon (IL)

(73) Assignee: FRESHPOINT QUALITY ASSURANCE LTD., Nesher (IL)

( * ) Notice: Subject to any disclaimer, the term of this patent is extended or adjusted under 35 U.S.C. 154(b) by 597 days.

(21) Appl. No.: 12/577,191

(22) Filed: Oct. 11, 2009

(65) Prior Publication Data

US 2011/0084128 A1 Apr. 14, 2011
US 2013/0105564 A9 May 2, 2013

Related U.S. Application Data

(63) Continuation of application No. 10/579,492, filed as application No. PCT/IL2004/001070 on Nov. 21, 2004, now abandoned.

(Continued)

(51) Int. Cl.
*G06F 17/00* (2006.01)
*G01K 3/04* (2006.01)
(Continued)

(52) U.S. Cl.
CPC ............ *G01K 3/04* (2013.01); *G01K 15/007* (2013.01); *G01N 31/229* (2013.01)

(58) Field of Classification Search
CPC ........... G01N 21/6428; G01N 21/6452; G01N 2800/2828; G01N 33/576; G01N 15/1475; G01N 2021/0346; G01N 2021/6432; G01N 2021/6439; G01N 2021/6441; G01N 2021/6482; G01N 21/05; G01N 21/6458;
(Continued)

(56) References Cited

U.S. PATENT DOCUMENTS 3,591,810 A 7/1971 Jackson
4,382,700 A 5/1983 Youngren
(Continued)

FOREIGN PATENT DOCUMENTS

EP 0276335 3/1988
EP 898202 2/1999
(Continued)

OTHER PUBLICATIONS

Eduardo et al.; (1991); -; J. Appl. Polymer Science; 71: 259-266.
(Continued)

*Primary Examiner* — Thien T Mai
(74) *Attorney, Agent, or Firm* — Browdy and Neimark, PLLC (57) ABSTRACT

A device is presented for use in controlling the quality of a perishable object, while progressing on its supply line, by monitoring the condition of a time-temperature indicator (TTI) associated with the object. The device comprises a sensing assembly for detecting a response of the TTI to a predetermined stimulus and generating measured data representative thereof, said measured data being indicative of the condition of the TTI, thereby enabling the determination of the remaining shelf life of the TTI and thereby any perishable good to which it is attached and calibrated.

23 Claims, 5 Drawing Sheets

Related U.S. Application Data (60) Provisional application No. 60/523,331, filed on Nov. 20, 2003.

(51) Int. Cl.
  *G01K 15/00* (2006.01)
  *G01N 31/22* (2006.01)

(58) Field of Classification Search
  CPC . G01N 2333/59; G01N 2800/52; G01N 33/48
  USPC .................. 235/375, 487; 116/207, 206, 219
  See application file for complete search history.

(56) References Cited

U.S. PATENT DOCUMENTS

| | | | |
|---|---|---|---|
| 4,432,656 A | | 2/1984 | Allmendinger |
| 4,737,463 A | * | 4/1988 | Bhattacharjee et al. ...... 116/206 |
| 4,773,766 A | | 9/1988 | Nagasaka et al. |
| 4,816,634 A | | 3/1989 | Lentz et al. |
| 4,834,017 A | * | 5/1989 | Favetto et al. ................ 116/206 |
| 4,859,360 A | | 8/1989 | Suzuki et al. |
| 5,053,339 A | * | 10/1991 | Patel ............................ 116/207 |
| 5,057,434 A | * | 10/1991 | Prusik .................... B65D 79/02 116/207 |
| 5,254,473 A | * | 10/1993 | Patel ............................ 116/216 |
| 5,317,987 A | | 6/1994 | Muller et al. |
| 5,667,303 A | * | 9/1997 | Arens et al. .................. 116/219 |
| 5,722,317 A | | 3/1998 | Ghiron et al. |
| 5,747,225 A | | 5/1998 | Manico et al. |
| 5,849,651 A | * | 12/1998 | Takayama ............ B41M 5/3375 503/201 |
| 5,969,606 A | | 10/1999 | Reber et al. |
| 6,009,400 A | | 12/1999 | Blackman |
| 6,042,264 A | | 3/2000 | Prusik |
| 6,242,714 B1 | | 6/2001 | Narumiya et al. |
| 6,382,125 B1 | * | 5/2002 | Tamura .................... B41M 5/28 116/207 |
| 6,435,128 B2 | | 8/2002 | Qiu |
| 6,514,462 B1 | | 2/2003 | Simons |
| 6,544,925 B1 | | 4/2003 | Prusik et al. |
| 6,614,728 B2 | | 9/2003 | Spevacek |
| 6,616,332 B1 | | 9/2003 | Renken et al. |
| 6,660,345 B2 | | 12/2003 | Coates et al. |
| 6,801,477 B2 | | 10/2004 | Braunberger |
| 6,822,931 B2 | | 11/2004 | Braunberger |
| 6,865,516 B1 | | 3/2005 | Richardson |
| 6,866,417 B2 | | 3/2005 | Gunawardena et al. |
| 6,974,249 B1 | | 12/2005 | Fair et al. |
| 7,039,927 B2 | | 5/2006 | Constantinou et al. |
| 7,081,364 B1 | | 7/2006 | Haarer et al. |
| 7,213,967 B2 | | 5/2007 | Simunovic et al. |
| 7,263,501 B2 | | 8/2007 | Tirinato et al. |
| 7,290,925 B1 | | 11/2007 | Skjervold et al. |
| 7,476,874 B2 | | 1/2009 | Patel |
| 7,600,912 B2 | | 10/2009 | Leute et al. |
| 8,183,045 B2 | | 5/2012 | Faran |
| 8,267,576 B2 | | 9/2012 | Haarer et al. |
| 8,277,749 B2 | | 10/2012 | Levy et al. |
| 8,343,437 B2 | | 1/2013 | Patel |
| 8,968,662 B2 | | 3/2015 | Haarer et al. |
| 2002/0056751 A1 | | 5/2002 | Lee |
| 2002/0085164 A1 | | 7/2002 | Stanford-Clark |
| 2003/0139843 A1 | | 7/2003 | Hu et al. |
| 2003/0174263 A1 | | 9/2003 | Lawandy |
| 2003/0193987 A1 | | 10/2003 | Zalameda et al. |
| 2004/0092023 A1 | | 5/2004 | Wright |
| 2004/0182932 A1 | | 9/2004 | Kawai |
| 2005/0037498 A1 | | 2/2005 | Ribi |
| 2005/0139686 A1 | * | 6/2005 | Helmer et al. ................ 235/487 |
| 2005/0178841 A1 | | 8/2005 | Jones et al. |
| 2005/0261991 A1 | * | 11/2005 | Kennamer ........... G06Q 10/087 705/28 |
| 2006/0032427 A1 | | 2/2006 | Ishii et al. |
| 2006/0203882 A1 | | 9/2006 | Makela et al. |
| 2007/0172951 A1 | | 7/2007 | Levy |
| 2008/0129037 A1 | | 6/2008 | Roth et al. |
| 2008/0187021 A1 | | 8/2008 | Haarer et al. |

FOREIGN PATENT DOCUMENTS

| | | | |
|---|---|---|---|
| JP | | 10046072 A | 2/1998 |
| JP | | 10334171 A | 12/1998 |
| WO | | WO 94/27242 | 11/1994 |
| WO | | WO 99/39197 | 5/1999 |
| WO | | WO 03/044521 | 5/2003 |
| WO | | WO 03/077227 | 9/2003 |
| WO | | WO 2004/077002 | 9/2004 |
| WO | | WO 2005/050192 | 6/2005 |
| WO | | WO 2005050192 A1 * | 6/2005 |
| WO | | WO 2005/075978 | 8/2005 |
| WO | | WO 2006/048412 | 5/2006 |
| WO | | WO 2008/083926 | 7/2008 |

OTHER PUBLICATIONS

International Search report for PCT/EP07/064595 dated Apr. 4, 2008.

International Search report for PCT/EP2009/057334 dated Oct. 2, 2009.

International Search report for PCT/IL2004/001070 dated Mar. 4, 2005.

* cited by examiner

METHOD AND SYSTEM FOR DETERMINING THE CONDITION OF A TIME-TEMPERATURE INDICATOR

This application is a continuation application of, and claims priority from, U.S. patent application Ser. No. 10/579,492, filed on May 16 2006 now abandoned, which claims priority from, and is a national stage application of, PCT Application No. PCT/IL04/01070, filed on 21 Nov. 2004, which claims priority from U.S. Provisional Application No. 60/523,331, filed on 20 Nov. 2003.

FIELD OF THE INVENTION

This invention is generally in the field of sensing techniques and relates to a system and method for determining the condition of a time-temperature indicator (TTI).

BACKGROUND OF THE INVENTION

The safety and quality of many perishable goods such as food, drugs, vaccines and blood, depend mainly on appropriate handling during distribution and storage. Different factors such as gas composition, relative humidity and temperature affect the effective lifetime of perishable goods. Of all storage aspects, temperature abuse is the most frequently observed factor for deterioration, based on diverse physical, chemical, enzymatic or microbial processes.

Time temperature indicators (alternatively called "Time temperature integrators") are devices (typically labels) with changeable observable physical property in a rate that is proportional to the temperature and time, and thus provide an indication of the full time-temperature history of their immediate surroundings. When attached to a perishable good, a TTI (appropriately designed and calibrated) monitors its time-temperature history and provides a simple, usually visual, indication of its freshness condition.

One example of a TTI is disclosed in U.S. Pat. No. 4,737,463. Another example is the TTI developed in part by the one inventor of the present invention and described in WO 99/39197.

U.S. Pat. No. 6,009,400 discloses a method and arrangement for alerting customers from purchasing perished items using bar codes with changeable properties when subjected to factors causing perishability. This technique is aimed at preventing retail establishment customers from unwittingly purchasing perishable items that may have been adversely affected by being subjected to at least one predetermined factor. This is achieved by providing an identification object, such as a label, tag or packaging material, with an initially machine-scannable bar code of such a character that its scannability is at least gravely impaired when the identification object is subjected to the predetermined factor. The identification object is secured to the respective item for both of them to be subsequently exposed to the same conditions such that a failed scan of the bar code occurring at the time of purchase alerts the customer to a previous occurrence among such conditions of the predetermined factor that may have adversely affected the item being purchased. In another aspect, a non-readable bar code is rendered readable by exposure to the predetermined factor, thereby alerting the customer.

SUMMARY OF THE INVENTION

There is a need in the art to facilitate determination of the freshness condition of a product by providing a novel device and method that allows for more quantitative assessment of freshness all along the supply chain, rather than a simple "Yes"/"No" visual readout. At different critical points along the supply chain, especially when the responsibility on the goods changes hands, a more quantitative assessment of the remaining shelf life of the products is desired.

The present invention takes an advantage of the property of a TTI to provide an effective "clear cut" answer that does not require further data inspection. This is ideal for cases where the emphasis is on real time decision-making and action.

The present invention provides for controlling the TTI condition, and consequently the condition of an object said TTI is associated with, while progressing on a supply chain. The technique of the present invention also provides for a simple and inexpensive device that is capable of effectively and quantitatively reading passive time-temperature integrating devices, thereby allowing for a continuous control of the TTI condition thus assessing the remaining shelf life of a perishable good along its supply chain.

According to one broad aspect of the present invention, there is provided a device for use in controlling the quality of a perishable object while progressing on its supply line by monitoring the condition of a time-temperature indicator (TTI) associated with the object, the device comprising a sensing assembly for detecting a response of the TTI to a predetermined stimulus and generating measured data representative thereof, said measured data being indicative of the condition of the TTI, thereby enabling the determination of the remaining shelf life of the TTI and thereby any perishable good to which it is attached and calibrated.

It should be noted that the term "controlling" used herein signifies also at least one of such functions as monitoring and tracking. The term "stimulus" signifies an external field, which when applied to the active region of a TTI, causes a detectable response of the active region indicative of the TTI condition.

Preferably, a light response of the TTI to predetermined incident light is detected. The light response may be in any form of spectrally resolved and/or non resolved data, intensity and/or changes in intensity of returned, absorbed and/or transmitted light, change in the refraction index, luminescence or certain color saturation or any other measurable quantity related to the electronic response of the active material in the TTI. The light response is detected by collecting reflections of incident light and/or emission of light excited by the incident light from the illuminated region of the TTI, or collecting light transmitted through the TTI. The stimulus (e.g., incident light) is predetermined in accordance with the type of the TTI, and may for example be in UV, visible or IR spectral range.

The sensing assembly thus comprises a source of stimulating field (e.g., light source generating the predetermined incident light), and a detector assembly (e.g., photodetector), and may comprise a control unit as its constructional part or be connected to a stand alone control unit via wires or wireless signal communication.

According to another broad aspect of the present invention, there is provided an optical probe for determining the condition of a time-temperature indicator (TTI), the probe comprising an optical sensing assembly for detecting a light response of the TTI to predetermined incident light and generating measured data representative thereof; and a communication utility for translating said data into an output signal in the form of at least one of electrical, optical, RF and acoustic signal, to be processed to determine the condition of the TTI, thereby enabling controlling and/or monitoring and/or tracing remaining shelf life of the TTI.

According to yet another broad aspect of the invention, there is provided a system for controlling an object, associated with a time-temperature indicator (TTI), while progressing on a supply line, the system comprising:

a sensing assembly for detecting a response of the TTI to a predetermined stimulus and generating measured data representative thereof, said measured data being indicative of the condition of the TTI, a control unit connectable to said sensing assembly and preprogrammed to be responsive to the measured data for translating said data into a value corresponding to the measured condition of the TTI, said measured condition of the TTI being indicative of remaining shelf life of the TTI and consequently of the object said TTI is associated with.

The freshness status of the perishable good may be expressed in its remaining lifetime at a given temperature. This data may be useful in supply line regulation and enforcement of such regulations, as well as for correlating deviations from regulations to specific segments of it using for example a simple inspection protocol. Such an inspection protocol can be performed on a normal TTI. All along the supply chain (i.e., at each or some of the supply chain nodes), the readout from the TTI is performed in a quantitative or semi-quantitative manner, using the above-described device, while at the end point of the chain, the end customer can visually inspect the TTI for making a YES/NO decision. Alternatively and/or additionally, the TTI condition can be controlled all along the supply chain by incorporating at least one TTI within a machine readable code (e.g., barcode) containing also other object-related data. This allows for continuously or periodically monitoring the object condition progressing on a supply chain. The present invention allows for extracting quantitative values from the TTI reading devices that are designed to give a YES/NO answer to the end customer.

The device of the present invention may be in the form of a barcode reader for reading a pattern having at least one patterned feature in the form of a TTI. The pattern may be provided on a label, tag or packaging material, which will be termed hereinbelow as "label".

The present invention, according to its yet another aspect, provides a label, tag or packaging material comprising a machine readable pattern having at least one feature of the pattern configured as a time-temperature indicator (TTI), said pattern being responsive to a predetermined stimulus in a time-temperature variable manner in accordance with time-temperature variations of the TTI.

Yet another aspect of the present invention provides for an object carrying a machine readable pattern that includes at least one feature of the pattern configured as a time-temperature indicator (TTI), said pattern being responsive to a predetermined stimulus in a time-temperature variable manner in accordance with time-temperature variations of the TTI.

The invention also provides a method for use in controlling an object while progressing on a supply chain, the object being associated with a time-temperature indicator (TTI), the method comprising:

at a node of the supply chain, detecting a response of the TTI to a predetermined stimulus and generating measured data representative thereof, processing said measured data to determine the condition of the TTI, thereby enabling determination of remaining shelf life of said TTI, thus enabling to define the object progress to a further node of the supply chain.

The supply chain should have a standard temperature but this is never maintained due to different reasons. The present invention provides for using a handshake protocol to enforce all the parties that are involved in the chill chain supply line to obey the rules. At each point (node of the supply chain), where there is a change in hands that hold the goods, and in any desired point, the TTIs are inspected, and the readout from the TTI provides the remaining shelf life according to the standard storage temperature. The receiving party thus may not accept the perishable good unless it has adequate remaining shelf life.

The preset handshake protocol may for example define, for each point where a product changes hands, a nominal (plus minimal and maximal) color condition. Hence, at each point of the supply line, the detected difference between the actual TTI condition and the predetermined condition gives indication of the remaining shelf life at a given temperature.

The present invention thus provides for assessing the remaining shelf life of a perishable good. This technique relies on calibrating a color-changing TTI, such as those produced by Lifelines or that developed in part by one inventor of the present invention and disclosed in WO 99/39197. At selected and/or arbitrary points along the goods' supply chain, and, specifically, at points along the supply chain in which changes of responsibility to the goods take place, the technique of the present invention is used to analyze the color status of the TTI that is attached to the perishable good. The color status of the TTI is then used to assess the condition, e.g. the freshness status, of the perishable good relaying on the specific calibration curves of the TTI, thus providing a means to evaluate the remaining effective shelf life at a given temperature.

BRIEF DESCRIPTION OF THE DRAWINGS

In order to understand the invention and to see how it may be carried out in practice, preferred embodiments will now be described, by way of non-limiting example only, with reference to the accompanying drawings, in which.

DETAILED DESCRIPTION OF THE INVENTION

Figure 1:
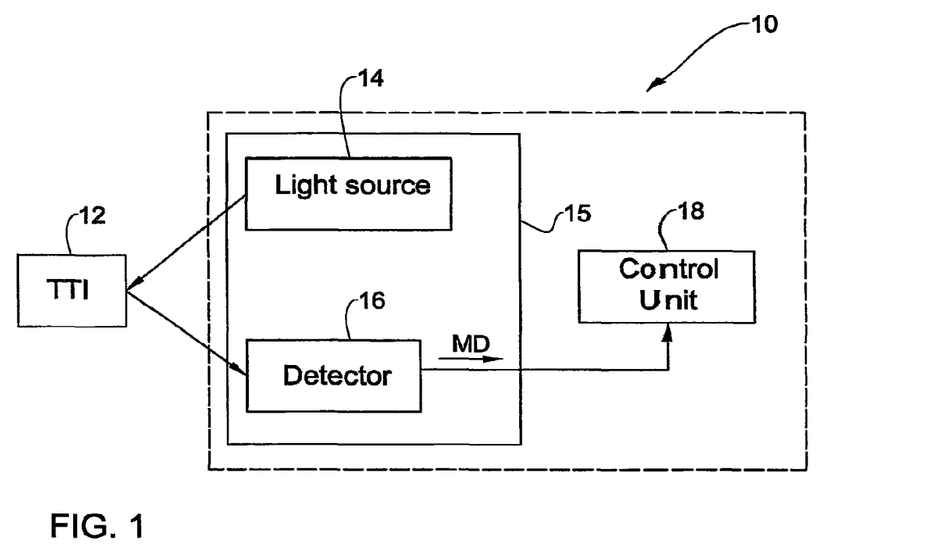
FIG. 1 is a block diagram of a device according to one embodiment of the invention.

Referring to FIG. 1, there is illustrated by way of a block diagram a device 10 according to one embodiment of the invention for use in determining the condition of a time-temperature indicator (TTI) 12. The device 10 is configured for detecting a response (light response in the present example) of the TTI to predetermined incident light (constituting an external field or stimulus) and generating measured data MD representative thereof. This measured data is indicative of the condition of the TTI and is thus indicative of the condition of an object (not shown) the TTI is associated with.

The device 10 comprises a light source 14; and a light detector 16. A control unit 18 is provided being connectable to the output of the detector, and preferably also connectable to the light source for operating the same. The light source and detector are housed in a chamber 15 designed to appropriately diffuse the incident light in a manner that it will homogeneously irradiate the active point (active region) of the TTI, as well as to direct the collected light response, originating from the active point, to the detector. The detector 16 is accommodated so as to collect the response of the TTI (e.g., reflection of the incident light, excited light, or light transmitted through the TTI). The light source 14 is of the kind generating incident light of a predetermined spectral range in accordance with the TTI type. For example, this may be a flash lamp operating in the visible spectrum. The spectral properties of the incident light beam and the collected light are electronically transferred to the control unit 18 through an interconnecting cable (or wireless transmission).

The control unit 18 is an electronic module including inter alia a memory utility, a data processing and analyzing utility, and a data presentation utility (e.g., display, indicator). The memory utility stores certain reference data including inter alia the spectral data and calibrated time-temperature color profile. The reference data may include information regarding various types of TTI. The data processing and analyzing utility is preprogrammed to be responsive to the measured data to determine the optical properties of the active point of the TTI and thus determine the condition of the TTI, and generate an output signal indicative thereof. This output signal is then appropriately formatted to be presented to the user via the data presentation utility (including one or more output ports).

It should be noted that the device energy needed to operate the device 10 is supplied by an energy source (not shown) that may be a battery or any other electrical source.

It should also be noted that the technique of the present invention is not limited to any specific type of the TTI and can be used for automatically monitoring the condition of any TTI. The type and operating parameters of the stimulus are selected in accordance with the TTI type.

An example of a photoactivated TTI that may be used in the device of the present invention is that produced by Lifelines, as disclosed in U.S. Pat. No. 4,737,463. According to this patent, a thermally inactive diacetylenic salt (or a mixture of such salts) is mixed, in a polymeric matrix, with a material that generates acid upon exposure to light. Photoexcitation causes the formation of a thermal active free diacetylenic acid. Following this activation step, a progressive color development occurs at a rate that increases with temperature. Another example is the TTI developed in part by one inventor of the present invention and described in WO 99/39197. According to this technique, a planar time-temperature integrator consisting of a matrix and at least one reversible indicator embedded therein is arranged in the area of the substrate. The indicator has photochromic properties based on transfer reactions. On the basis of such properties, the indicator is coloured in photoinduced manner and a time-dependent and temperature-dependent discolouration occurs. The degree of time-related or temperature-related discolouration is measured and the product quality is concluded therefrom.

Figure 2:
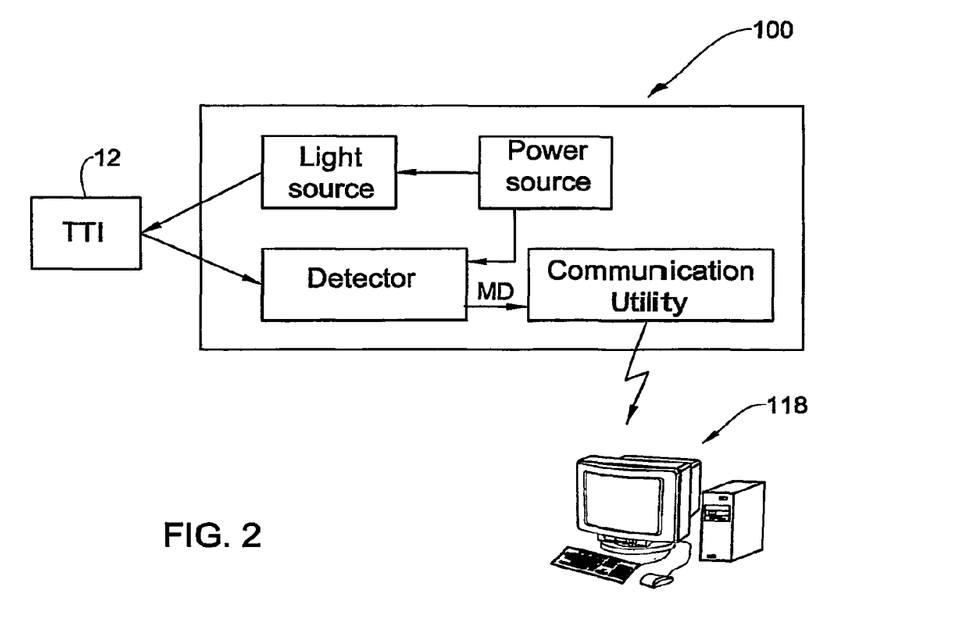
FIG. 2 is a block diagram of a device according to another embodiment of the invention.

FIG. 2 illustrates a device 100 according to another example of the present invention. To facilitate understanding, the same reference numbers are used for identifying those components which are similar in the examples of FIGS. 1 and 2. In this example, the device 100 is in the form of a hand-held optical probe including a light source 14, a photodetector 16, a battery 17, and a communication utility 20. The communication utility 20 is connected to the output of the photodetector for receiving measured data MD representative of the detected light response of a TTI, and is appropriately configured for translating the measured data into an output signal of the kind to be wirelessly transmitted to a stand-alone control unit 118. This output signal may be RF, IR or acoustic signal. The control unit 118 is thus equipped with a suitable communication utility for communicating with the device 100.

Figure 3:
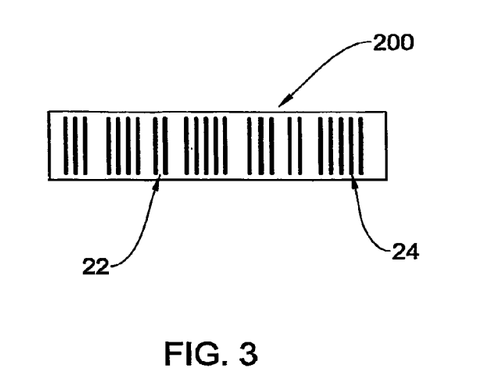
FIG. 3 is a schematic illustration of a label attachable to an object and carrying a barcode-like pattern with at least one TTI.

Reference is now made to FIG. 3 illustrating an optically readable pattern 22 (e.g., barcode), which is configured to be representative of object-related information and has at least one feature in the form of a TTI 24. This pattern 22 is printed on a substrate 200 that may be a label, tag or packaging material, or may be the object itself.

The pattern 22 is thus representative of the object-related data, including data indicative of the object's remaining shelf life at a given temperature. Collecting a light response of the pattern 22 (e.g., by scanning the pattern) allows for reading the object-related information and detecting the condition of the TTI, and thus detecting the freshness condition of the object. In this case, a suitable barcode reader may include the sensor device of the present invention as described above and as exemplified in FIGS. 1 and 2. The sensor device (or stand alone control unit associated with the sensor device) is appropriately preprogrammed with a certain protocol for determining, from the response of the TTI, the remaining shelf life of this TTI, and generating an output signal indicative thereof, thus enabling to either accept or reject the product.

Figure 4:
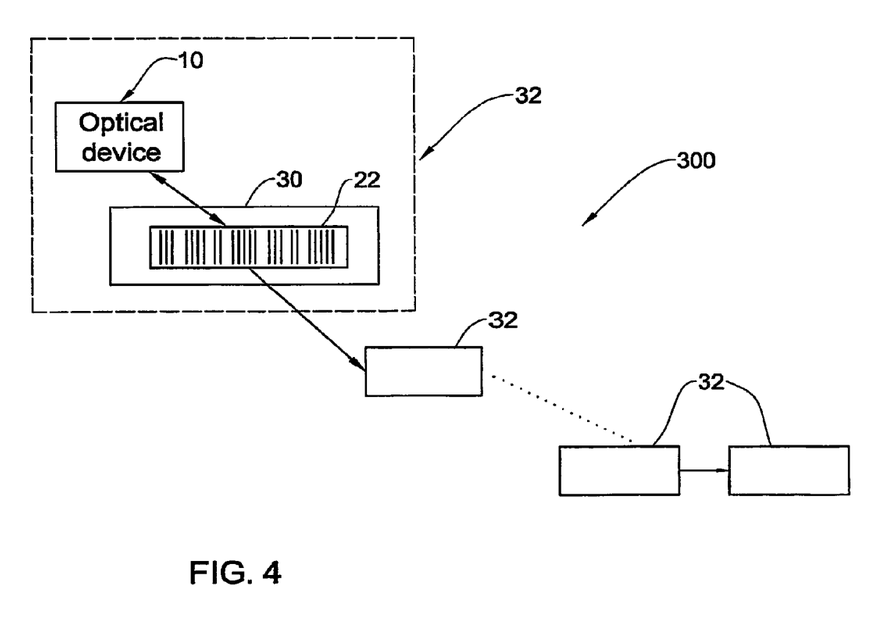
FIG. 4 schematically illustrates an objects' supply chain including a plurality of nodes (points) each utilizing the device of the present invention for determining the object condition when arriving at the chain node.

FIG. 4 shows how the present invention can be used for monitoring the object condition while progressing on a supply line. The freshness status of the perishable good may be expressed in its remaining lifetime at a given temperature. This data may be useful in supply line regulations as well as correlating deviations from regulations to specific segments of it. FIG. 4 schematically illustrates an object 30 while progressing on a supply chain 300. The object 30 carries a TTI or a pattern 22 (machine readable code) including TTI-related pattern feature(s). The TTI or the pattern with TTI is printed on the object or on a label/tag attached to the object, or the object packaging material. The supply chain 300 includes several nodes, generally at 32, each utilizing the TTI/pattern reading device of the present invention (for example device 10 or 100 exemplified above) for detecting the TTI condition (and thus the object condition) when arriving at said node.

The predetermined TTI condition varies from point to point of the chill chain supply line which can be monitored in accordance with a preset handshake protocol. This protocol may define for each point (node) where a product changes hands, a nominal (plus minimal and maximal) color condition. Hence, at each point of the supply line, the detected current condition of the TTI gives indication of the remaining shelf life of the TTI at a given temperature.

Figure 5A:
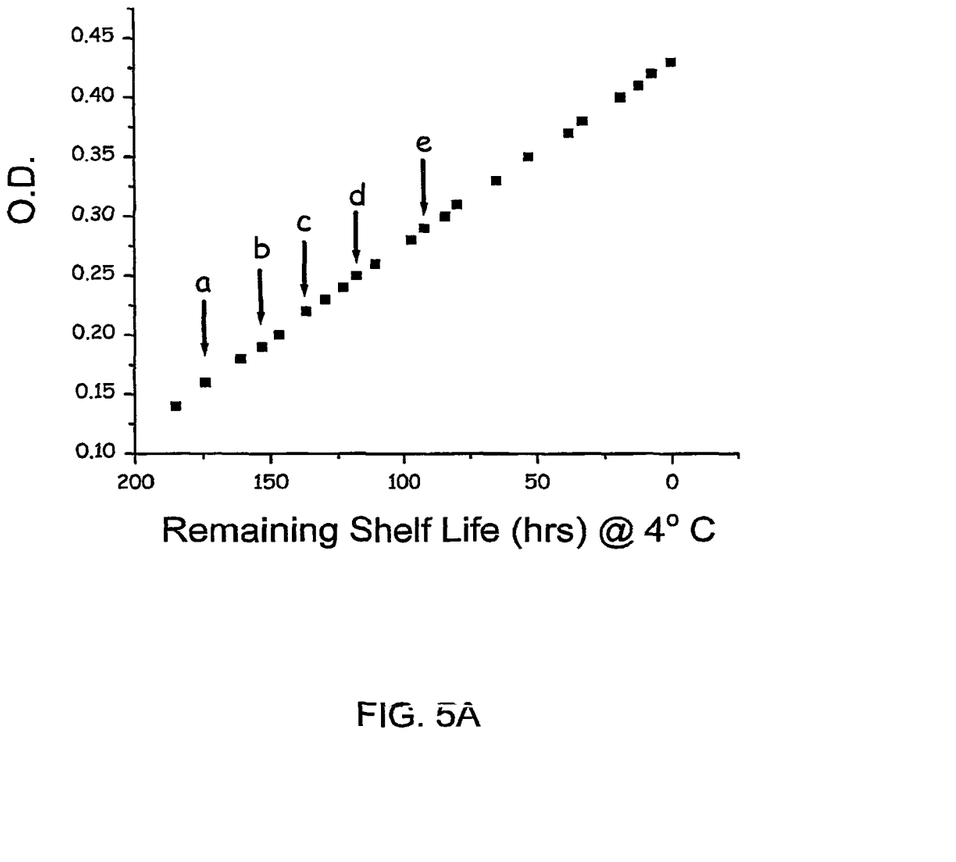
FIGS. 5A and 5B illustrate two examples, respectively, of the time variation of responses from different types TTIs at respective standard temperature conditions.

FIG. 5A shows the time response of "Fresh Check" TTI (produced by Lifelines) at 4° C. The active matrix of the TTI changes its color from light to dark, in a process that at 4° C. takes 185 hours. The points in the graph of FIG. 5A represent values corresponding to the readings obtained from the TTI at different time intervals, starting when bringing the TTI to a temperature of 4° C. from its storage temperature, thus setting its "time zero". Along the lifespan of the TTI, the color of the TTI active matrix progresses in a predictable fashion as a function of the time.

Figure 5B:
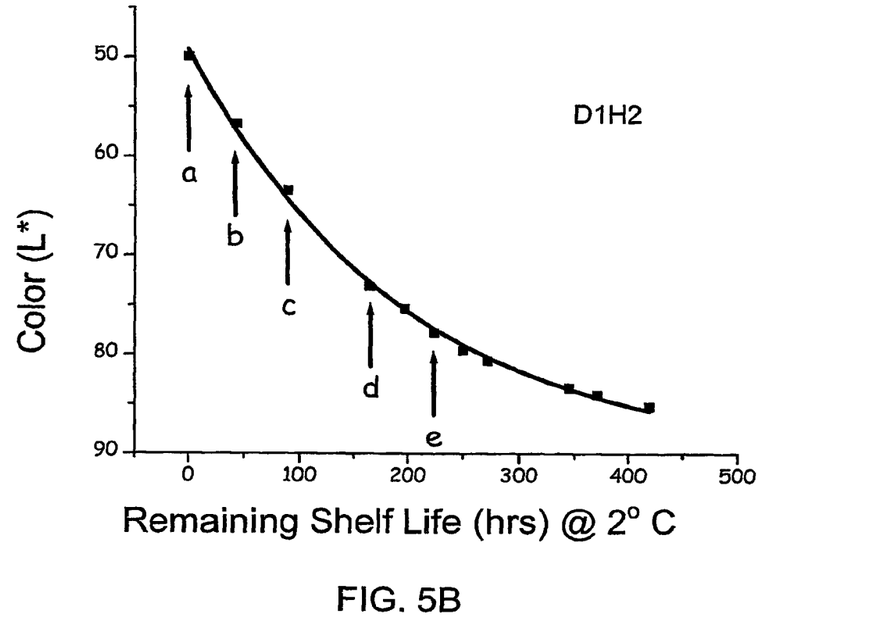

FIG. 5B shows the time response of the ITT of another type (developed in part by one inventor of the present invention and disclosed in WO 99/39197) at 2° C. The active matrix of the TTI changes its color from dark blue to white, in a process that at 2° C. takes 500 hours. The points in the graph represent the values of readings of the TTI response at different time intervals after charging the TTI using UV light, thus setting its "time zero". Along the TTI lifespan, the color of the active matrix of the specific TTI progresses in a predictable fashion as a function of the time.

Figure 6:
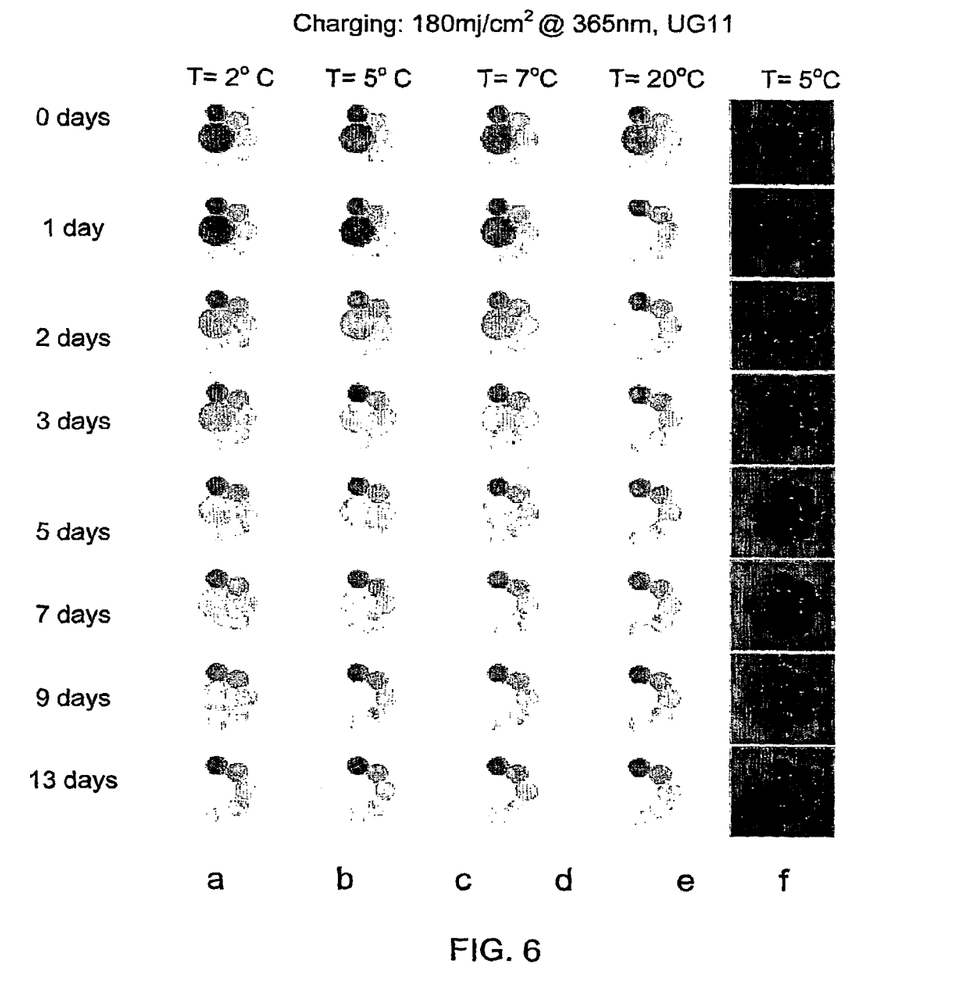
FIG. 6 more specifically illustrates the time variations of the TTI condition at different temperatures.

FIG. 6 more specifically illustrates the time-temperature behavior of this TTI (being sensed as the TTI response to 365 nm incident radiation). Positions a to d correspond to the TTI variations during the time period of 13 days under the temperature conditions of, respectively, 2° C., 5° C., 7° C. and 20° C., and position e shows the TTI conditions of position b but obtained using a green filter. As shown, the color of the TTI active matrix varies in a predictable fashion from dark blue to white as a function of the time and temperature.

The following are two specific, but not limiting, examples of using the chill chain handshake protocol in accordance with the present invention for controlling the TTI condition (i.e., the object condition) all along the supply chain.

Example 1

In this example, the TTI used for demonstrating the monitoring and control of the chill chain using a handshake protocol in accordance with the present invention, is the "Fresh Check" Time Temperature Indicator produced by Lifelines. The specific time response of this TTI at 4° C. is shown in FIG. 5A.

In a simulation of a chill chain condition, the TTI is transferred from one person (node of the chain) to another in a way that none of them could know the time-temperature history of the TTI prior to the time point he received the TTI. Each of the participants is equipped with a reading device of the present invention appropriately calibrated to the specific TTI for reading data indicative of the TTI (or the entire pattern including the TTI-feature).

The standard conditions of the specific chill chain determined for the experiment are as follows: Each party (at each node of the chain) is entitled to refuse acceptance of the goods transported along the chill chain, if the remaining standard shelf life (RSSL) is shorter than a certain minimal value. This is depicted in Table 1 exemplifying the minimal remaining standard shelf life (MRSSL) at 4° C.:

TABLE 1

| Station | Remaining standard shelf life (hrs) Minimum | Maximum Color |
|---|---|---|
| a | 180 | 0.17 |
| b | 160 | 0.20 |
| c | 128 | 0.23 |
| d | 109 | 0.26 |
| e | 83 | 0.30 |

First experiment—a TTI (product with TTI) is kept at a constant temperature of 4° C. all along the experiment:

At the starting node a of the supply chain, user A (representing the company that produces the product) brings the TTI from its storage temperature to the 4° C. temperature, thus setting its "time zero". At that moment, user A measures the TTI response to incident light (e.g., the color of the TTI) in a manner described above, thus confirming that the response (color) of the TTI is lower than 0.17 O.D., corresponding to the MRSSL at 4° C. of 180 hours. The ITT then progresses on the supply chain to node b.

At node b, user B (representing the first transporter that transports the goods from the producer to the first warehouse) is responsible for controlling the goods' condition arriving from the producer (node a). Upon accepting the goods from user A, user B measures the response (color) of the TTI and detects that the color of the TTI is lower than 0.20 O.D., representing the minimal value (MRSSL at 4° C.) of 160 hours.

The product with TTI is then passed to node c. Here, user C (representing the warehouse), upon accepting the goods from user B, measures the ITT response (color), confirming that the color of the TTI is lower than 0.23 O.D., representing the minimal value (MRSSL at 4° C.) of 128 hours.

The product with TTI is then passed to node d where the second transporter is responsible for transporting goods from the warehouse to a supermarket store-room. Upon accepting the goods from user C, user D measures the color of the TTI, confirming that the color of the TTI is lower than 0.26 O.D., representing the MRSSL at 4° C. of 109 hours.

The product with TTI is then passed to node e, constituting the supermarket shelf. Upon accepting the goods from node d, user E at node e measures the color of the TTI, confirming that the color of the TTI is lower than 0.30 O.D., representing a MRSSL at 4° C. of 83 hours.

Second experiment—a TTI (product with TTI) is kept at a constant temperature of 4° C. all along the experiment, except for that of the warehouse, where the TTI is exposed for an unknown period of time to the room temperature.

At the starting node a, user A (a company that produces the product) brings the TTI from its storage temperature to a temperature of 4° C., thus setting its "time zero". At that moment, user A measures the color of the TTI, confirming that it is lower than 0.17 O.D., representing a MRSSL at 4° C. of 180 hours.

The product with TTI is then passed to node b representing the first transporter that transports the products from the producer to the first warehouse. Upon accepting the goods from node a, user B measures the color of the TTI, confirming that the color of the TTI is lower than 0.20 O.D., representing a MRSSL at 4° C. of 160 hours.

The product with TTI is then passed to node c, representing the warehouse. Upon accepting the goods from node b, user C measures the color of the TTI, confirming that the color of the TTI is lower than 0.23 O.D., representing a MRSSL at 4° C. of 128 hours. At this node, the TTI becomes exposed to the room temperature for an unknown period of time.

The product with TTI is then passed to node d representing the second transporter that transports the goods from the warehouse to the supermarket store-room. Upon accepting the goods from company c, user D measures the color of the TTI, expecting to detect whether the color is lower than 0.26 O.D., representing a MRSSL at 4° C. of 109 hours. However, the reading shows the color of 0.29 O.D. which represents a MRSSL at 4° C. of 109 hours. This is because the TTI has been exposed to the room temperature for an unknown period of time that occurred at node c.

The temperature abuse can now be easily correlated with company c since this company is delivering the product with TTI, the condition of which was in accordance with the standards until it reached node c and was found to exceed the maximal color at the supply chain between nodes c and d.

The protocol may thus allow the receiving party to refuse accepting goods having shorter than determined minimal remaining standard shelf life at a standard temperature. Alternatively, the protocol may serve to find failure points in such a chill chain or allow pricing of goods with respect to their minimal remaining standard shelf life at a standard temperature.

Example 2

In this example, the TTI used for demonstrating the monitoring and controlling of the chill chain using a handshake protocol in accordance with the present invention, is the Time Temperature Indicator developed in part by one inventor of the present invention and disclosed in WO 99/39197. The specific time variation of the TTI response at 2° C. is shown in FIG. 5B.

In a simulation of the chill chain condition, the TTI is transferred from one person (node) to another in a way that none of them could know the time-temperature history of the TTI prior to the time point the TTI is received at the specific node. Each of the participants is equipped with the TTI response reading device of the present invention, calibrated to the specific TTI.

The standard conditions of the specific chill chain determined for the experiment are as follows: Each party is entitled to refuse acceptance of the goods transported along the chill chain, if the remaining standard shelf life at 2° C. (MRSSL at 2° C.) is shorter than the minimal value, as depicted in Table 2.

TABLE 2

Minimal remaining standard shelf life at 2° C.

| Station | Remaining standard shelf life (hrs) Minimum | Maximum Color (L*) |
|---|---|---|
| a | 500 | 49 |
| b | 458 | 57 |
| c | 412 | 64 |
| d | 335 | 72 |
| e | 225 | 78 |

First experiment—the TTI is kept at a constant temperature of 2° C. all along the experiment.

At the starting node a (a company that produces the product), the TTI associated with the product is charged at a temperature of 2° C., thus setting its "time zero". At that moment, the TTI response (color) is measured (using the device of the present invention), confirming that the color of the TTI is higher than 49 L*, representing a MRSSL at 2° C. of 500 hours. The TTI is then allowed to pass to node b representing the first transporter that transports the goods from the producer to the first warehouse.

At node b, upon accepting the goods from node a, the color of the TTI is measured, confirming that the color of the TTI is higher than 57 L*, representing a MRSSL at 2° C. of 458 hours. The TTI is then passed to node c representing the warehouse.

At node c, upon accepting the goods from node b, the color of the TTI is measured, confirming that it is lower than 64 L*, representing a MRSSL at 2° C. of 412 hours. The TTI is then passed to node d representing the second transporter that transports the goods from the warehouse to the supermarket store-room.

At node d, upon accepting the goods from node c, the color of the TTI is measured, confirming that it is lower than 72 L*, representing a MRSSL at 2° C. of 335 hours. The TTI is then passed to node e, representing the supermarket shelf.

At node e, upon accepting the goods from node d, the color of the TTI is measured, confirming that it is lower than 78 L*, representing a MRSSL at 2° C. of 225 hours.

It should be understood that the main differences between Examples 1 and 2 are in the direction of the change in color: in Example 1 the TTI color changes from light to dark, while in Example 2—from dark to light; and in that the TTI of Example 2 is chargeable and may be charged at the precise desired time.

Second experiment of Example 2—the TTI is kept at a constant temperature of 4° C. all along the experiment, except for that in the warehouse, where the TTI is exposed to the room temperature for an unknown period of time.

At node a, the TTI color is sensed, confirming that it is higher than 49 L*, representing a MRSSL at 2° C. of 500 hours. The TTI is then passed to node b representing the first transporter that transports the goods from the producer to the first warehouse.

Upon accepting the goods from node a, user B at node b measures the color of the TTI, confirming that the color is higher than 57 L*, representing a MRSSL at 2° C. of 458 hours. The product with TTI is then passed to node c, representing the warehouse.

At the warehouse (node c), upon accepting the goods from node b, the color of the TTI is measured, confirming that the color is higher than 64 L*, representing a MRSSL at 2° C. of 412 hours. Here, the TTI becomes exposed to the room temperature for an unknown period of time. The TTI is then passed to node d, representing the second transporter that transports the goods from the warehouse to the supermarket store-room.

At the node d, upon accepting the goods from node c, the TTI is inspected to determine whether its color is higher than 72 L*, representing a MRSSL at 2° C. of 335 hours. The inspection shows the color to be of 84 L*, which corresponds to a MRSSL at 2° C. of only 155 hours. This is because at node c the TTI has been exposed to the room temperature for an unknown period of time. The temperature abuse can now be easily correlated with company c since this company is delivering a product with TTI that was in accordance with the standards until it reached node c and is found to exceed the maximal color when arrives to node d. Hence, here again, the protocol may allow the receiving party to refuse accepting goods having shorter than determined minimal remaining standard shelf life at a standard temperature, or alternatively, the protocol may serve to find failure points in such a chill chain or allow pricing of goods with respect to their minimal remaining standard shelf life at a standard temperature.

One more example of the technique of the present invention consists of using a normal TTI that is characterized by one reference scale that is available only to the parties involved in the product chill chain supply. These parties are thus allowed for carrying out the quantitative assessment of the TTI using this reference scale. As for the end customer, he can solely obtain a digital YES/NO reference scale. The reference scale available to the parties of the chill chain supply line is made with a transparent region or hole in the middle, and can be placed manually and temporarily onto the TTI, such that the chill chain reference scale covers the customers scale during the inspection at the nodes of the chill chain.

Those skilled in the art will readily appreciate that various modifications and changes can be applied to the embodiments of the invention as hereinbefore exemplified without departing from its scope as defined in and by the appended claims.

What is claimed is:

1. A system for monitoring a monitored object while progressing on a supply chain, the monitored object being a perishable good, the system comprising an identification object physically associated with the monitored object, wherein said identification object comprises a time-temperature indicator (TTI) to assess the freshness status of the perishable good, the system further comprising a plurality of nodes, the monitored object being monitored at a plurality of said nodes and the monitored object being progressed between said plurality of nodes forming the supply chain, wherein physical control of said monitored object changes at each node, each node comprising:
   a. sensing assembly for detecting a response of the TTI to a predetermined stimulus, which response is indicative of the full time-temperature history the TTI has experienced, and generating measured data representative of said response, such that said measured data is quantitatively indicative of the condition of the TTI, and thus the freshness status of the perishable good being monitored;
   b. a communication utility in communication with said sensing assembly for translating said measured data into an output signal providing a quantitative indication of the freshness status of the perishable good being monitored;
   c. a control unit, communicating with said communication utility, said control unit comprising a data processing and analyzing utility for determining the remaining shelf life of the monitored perishable good at a given temperature according to the value of said output signal received from said communication utility, the determination of remaining shelf life being accomplished without the requirement of knowledge of the starting time of the perishable good into the supply chain; and
   d. a controller for determining whether the remaining shelf life of the monitored object is sufficient for progressing the monitored object from a current node to a subsequent node in the supply chain according to a handshake protocol, wherein the monitored object is transferred from said current node to said subsequent node according to the remaining shelf life.

2. The system of claim 1, wherein said identification object is selected from the group consisting of a label, a tag and packaging material.

3. The system of claim 2, wherein said sensing assembly comprises a light source generating predetermined incident light, and a light detector, and wherein the detected response includes a light response of the TTI to said predetermined incident light.

4. The system of claim 3, wherein said light detector measures spectral data.

5. The system of claim 3, wherein said light response is in the form of certain color saturation.

6. The system of claim 3, wherein said light response includes reflections of the incident light.

7. The system of claim 3, wherein said light response includes light transmitted through the TTI.

8. The system of claim 3, wherein said incident light is in a visible spectral range.

9. The system of claim 8, wherein said light source is a flash lamp.

10. The system of claim 1, wherein said sensing assembly and said communication utility are located remotely from said control unit.

11. The system of claim 1, wherein the supply chain is a chill chain.

12. The system of claim 11, wherein said identification object is printed upon the monitored object itself.

13. The system of claim 11, wherein said communication utility produces said output signal in the form of at least one of electrical, optical, RF and acoustic signal.

14. The system of claim 1, wherein said identification object comprises a machine readable pattern, at least one feature thereof being configured as said TTI.

15. The system of claim 11, wherein said controller determines at least a minimum remaining shelf-life according to said handshake protocol, such that the monitored object is not progressed along the supply chain if said minimum remaining shelf-life is not met.

16. The system of claim 15, wherein said data processing and analyzing utility determines a quantitative measurement of said remaining shelf-life and wherein said controller determines at least said minimum remaining shelf-life according to said quantitative measurement.

17. The system of claim 16, wherein said controller determines at least a minimum shelf life according to said quantitative measurement.

18. The system of claim 17, further comprising a receiving party at an end node at the end of the supply chain, said receiving party determining whether to accept the monitored object.

19. The system of claim 18, wherein said receiving party comprises an end customer for purchasing the monitored object and for visually inspecting the TTI to determine the remaining shelf life at a given temperature according to said status of the TTI.

20. The system of claim 18, wherein said receiving party comprises a supermarket.

21. The system of claim 1, wherein said supply chain comprises a plurality of physically separated facilities, such that said plurality of nodes comprises at least two different physically separated facilities, wherein said controller determines whether the remaining shelf-life of the monitored object is sufficient for physically progressing the monitored object from a current node to a subsequent node in the supply chain.

22. The system of claim 14, wherein at least one node further comprises a machine-readable pattern reader for reading the pattern on said identifying object to identify the monitored object.

23. A system for monitoring a monitored object while progressing on a supply chain, the monitored object being a perishable good, the system comprising an identification object physically associated with the monitored object, wherein said identification object comprises a time-temperature indicator (TTI) to assess the freshness status of the perishable good, the system further comprising a plurality of nodes, the monitored object being monitored at a plurality of said nodes and the monitored object being progressed between said plurality of nodes forming the supply chain, wherein physical control of said monitored object changes at each node, each node comprising:
   a. sensing assembly for detecting a response of the TTI to a predetermined stimulus, which response is indicative of the full time-temperature history the TTI has experienced, and generating measured data representative of said response, such that said measured data is quantitatively indicative of the condition of the TTI, and thus the freshness status of the perishable good being monitored;
b. a communication utility in communication with said sensing assembly for translating said measured data into an output signal providing a quantitative indication of the freshness status of the perishable good being monitored;
c. a control unit, communicating with said communication utility, said control unit comprising a data processing and analyzing utility for determining the remaining shelf life of the monitored perishable good at a given temperature according to the value of said output signal received from said communication utility, the determination of remaining shelf life being accomplished without the requirement of data other than said output signal corresponding to said measured data; and
d. a controller for determining whether the remaining shelf life of the monitored object is sufficient for progressing the monitored object from a current node to a subsequent node in the supply chain according to a handshake protocol, wherein the monitored object is transferred from said current node to said subsequent node according to the remaining shelf life.

* * * * *